United States Patent [19]
Russo et al.

[11] Patent Number: 5,490,518
[45] Date of Patent: Feb. 13, 1996

[54] LEG LENGTH ANALYZER

[75] Inventors: Roger Russo, 6 Oak Ridge Ct., Pomona, N.Y. 10970; Paul Lauro, Nanuet, N.Y.

[73] Assignee: Roger Russo, Pomona, N.Y.

[21] Appl. No.: 372,965

[22] Filed: Jan. 17, 1995

[51] Int. Cl.[6] .................................................. A61B 5/103
[52] U.S. Cl. .......................................................... 128/774
[58] Field of Search .............................. 33/3 A, 3 B, 3 C, 33/3 R, 511, 512, 515; 128/774, 779, 782

[56] References Cited

U.S. PATENT DOCUMENTS

| | | | |
|---|---|---|---|
| 1,684,555 | 9/1928 | Ritholz | 33/3 A |
| 3,196,551 | 7/1965 | Provost et al. | |
| 3,520,293 | 4/1967 | Atherholt . | |
| 3,579,837 | 5/1971 | Soriano | 33/3 B |
| 4,603,486 | 8/1986 | Mooney et al. | 128/774 |
| 4,742,832 | 5/1988 | Kauffmann et al. | 128/774 |
| 4,939,849 | 7/1990 | Johnson | 33/512 |

*Primary Examiner*—Max Hindenburg
*Attorney, Agent, or Firm*—Stanley J. Yavner

[57] ABSTRACT

A leg length inequality measuring device is provided to quantitatively determine one of the signs of postural imbalance. The invention device is for use by chiropractic practitioners. Both legs are usually of the same length, but when the skeleton of a patient is out of alignment an appearance of differing leg lengths is presented, and the cause and treatment are decided by determining accurately if there is a difference in leg length. A convenient and reliable device for this purpose is in the form of a solid rectangle with stepped or V-shaped edge slots arranged with a pair of such slots running across the top surface thereof, and the other slot running perpendicular to the two cross-slots and along the length of the bottom face of the item. The two cross-slots are for accommodating sliding measuring slabs to various positions in order to determine the difference in leg length measurement for each leg, as the patient lies on his or her belly with heels against such slabs. The lengthwise slab for motion in the lengthwise slot is to accommodate, for instance, bulging thighs of the patient. Set screws are used to fix, when needed, the motion of the sliding slabs.

5 Claims, 3 Drawing Sheets

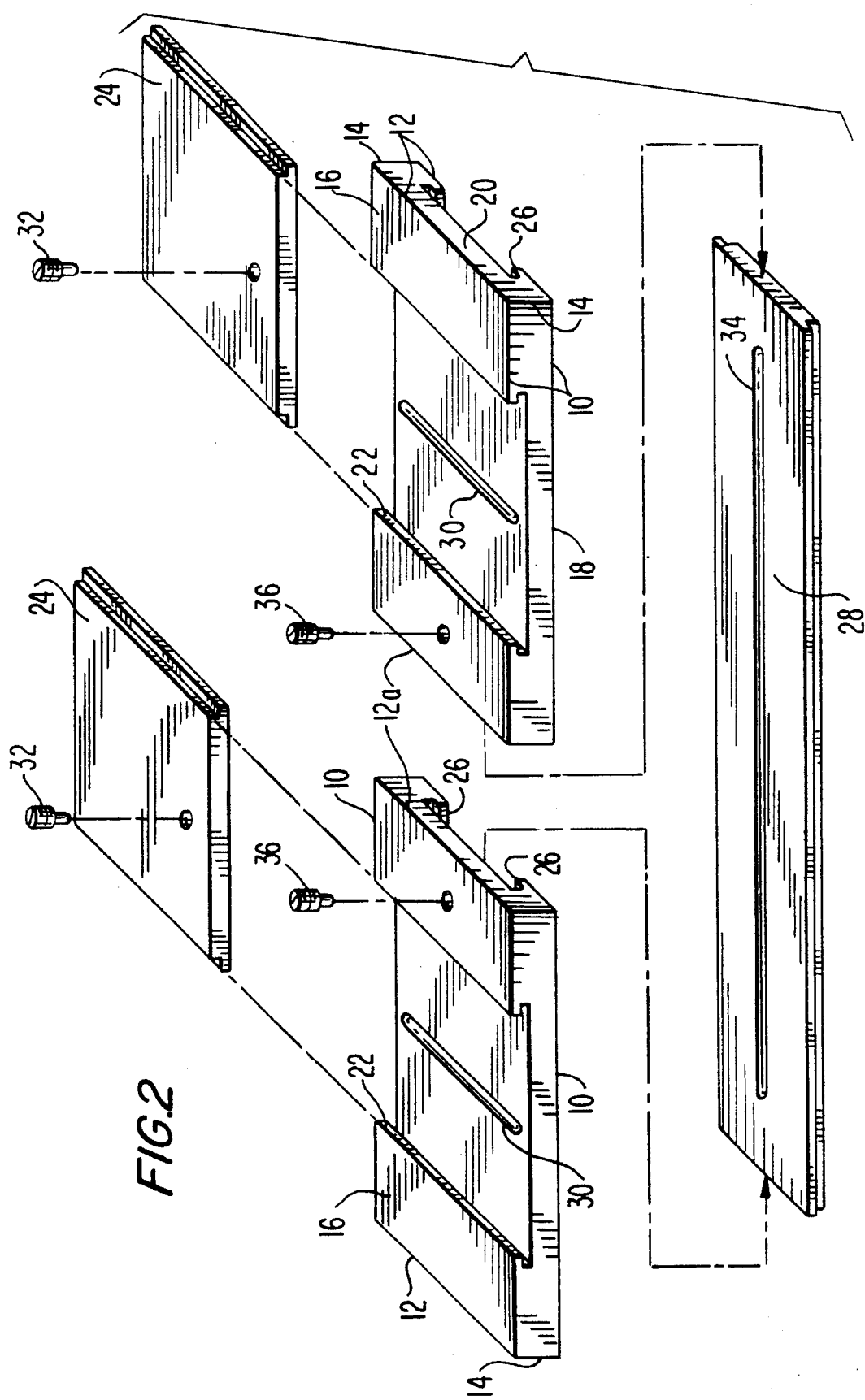

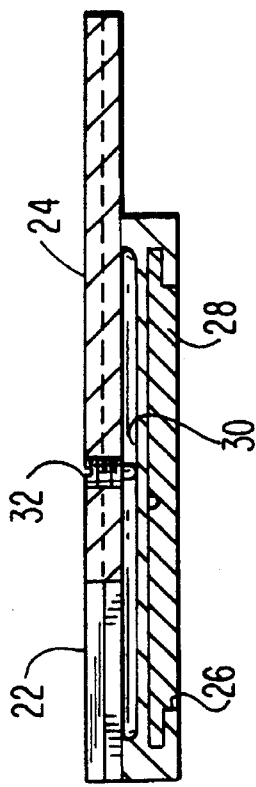
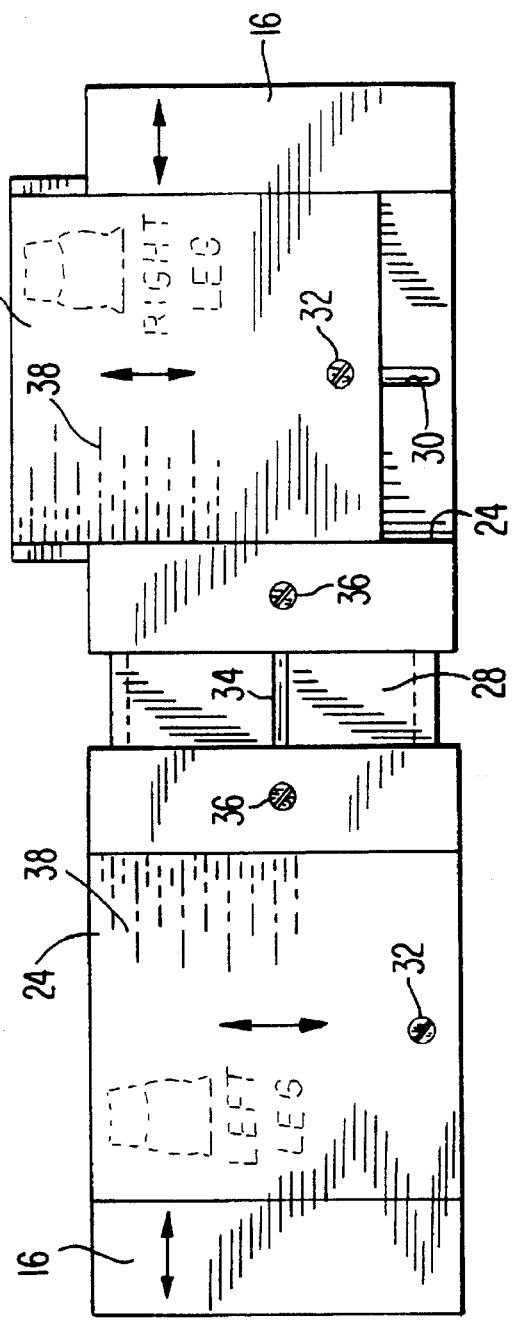

LEG LENGTH ANALYZER

FIELD OF THE INVENTION

This invention relates primarily to tools for the doctor of chiropractic, and more particularly to tools for measuring a difference between the leg lengths of a patient.

BACKGROUND OF THE INVENTION

An important analysis to be made by doctors of chiropractic relates to determining whether or not one of the patient's legs is shorter or longer than the other. A difference in leg lengths could mean that the skeleton is generally out of alignment or that a spinal problem exists.

Typically, the doctor of chiropractic, or any physical therapists and any orthopedic practioner, finds it critical to determine if a leg length difference exists, since, with either skeletal misalignment or spinal abnormality, the condition will get worse if untreated.

In present practice, various techniques and tools have been used for determining leg length differences. For instance, U.S. Pat. No. 3,520,293, invented by Atherholt, shows a device for measuring leg length differences by a rather complex device relying upon force measurements. U.S. Pat. No. 3,196,551 by Provost, et al, is similar in terms of its complexity for the same purpose.

In terms of eliminating complexity, most practitioners have avoided the complex devices and tools by using a hand-measurement test which has proven to be quite inaccurate. In the hand-measurement test, the patient lies on his belly and equal hand pressure is applied to pull the legs to their full length, and a difference is noted or measured by an assistant. In such cases, a check of the noted difference is performed by having the patient bend his or her knees and the comparison is again made by either noting the difference or the measurement.

OBJECTS AND SUMMARY OF THE INVENTION

Accordingly, a primary object of the present invention is to provide, primarily for chiropractic use, a simple tool for analyzing and measuring leg length differences to detect skeletal or spinal abnormalities.

A further and more particular object is to provide a tool which is simple, and yet reliable and efficient, in measuring leg length differences.

A stil further object of the present invention is to provide a tool for measuring and analyzing leg length differences which is convenient to use, accurate in its measurement and which can be used by a single diagnostician with accommodation for patients with bulging thighs.

These and other objects of the present invention are provided in a leg length analyzer tool for measuring differences in a patient's leg lengths. The tool is primarily in the shape and form of a solid rectangle with a plurality of length edges, a plurality of width edges and a plurality of thickness edges. Furthermore, as with any solid rectangle, there are upper and lower surfaces, end surfaces and side surfaces. One of the surfaces, the upper surface, defines cross-slots with stepped or V-shaped edges corresponding in length to the end surfaces of the solid rectangle. Each of the cross-slots accommodates a cross slab, defining measurement indicia on the upper face of the slab. The bottom surface of the solid rectangle defines a lengthwise slot having stepped or V-shaped edges for accommodating another slab so that the tool, with a sliding motion, can be separated at a point between the cross-slots in order to accommodating bulging thighs of a patient. As an alternative embodiment, set screws are used in order to limit motion of the various slabs.

BRIEF DESCRIPTION OF THE DRAWINGS

Other objects and advantages of the present invention will become apparent by reference to the following detailed description of a preferred and alternative, but nonetheless illustrative, embodiment of the present invention, with reference to the accompanying drawings, wherein:

FIG. 2 is a break-away view of the tool, according to the present invention illustrated in FIG. 1, the break-away view showing the various slabs removed from the main body of the tool;

FIG. 4 is a side sectional view, taken along the line 4—4 of FIG. 1; and

FIG. 5 is a top view of the tool according to the present invention, showing particularly the directional capability for the slabs, as well as the measurement indicia thereon.

DETAILED DESCRIPTION OF THE PREFERRED AND ALTERNATIVE EMBODIMENT

Figure 1:
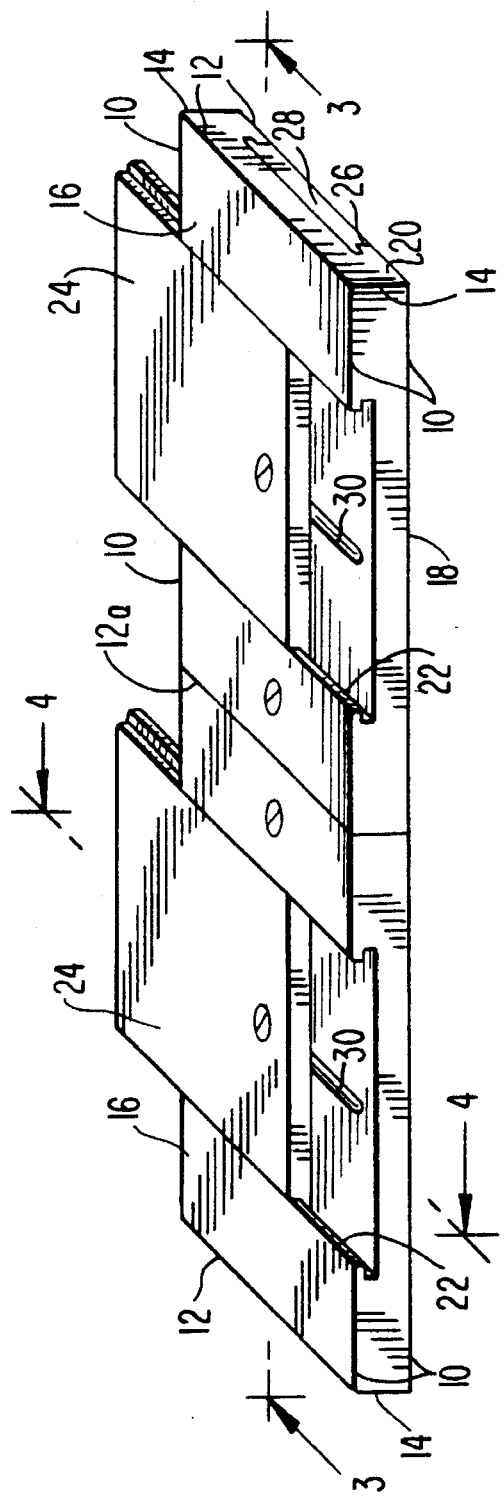
FIG. 1 is an isometric view showing primarily the upper surface of the solid rectangular tool, but also showing a side surface and an end surface thereof.
Figure 3:
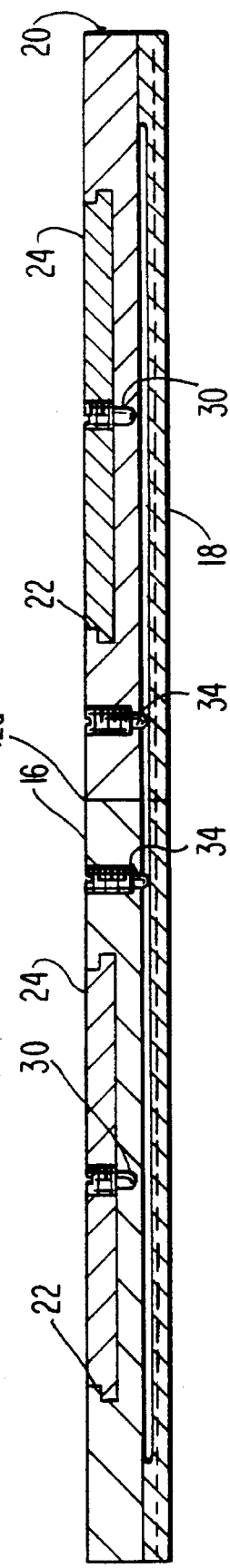
FIG. 3 is a front cross-sectional view of the tool of FIG. 1, taken along the line 3—3 thereof.

Referring to the drawings, and particularly FIGS. 1 and 2 thereof, the present invention is shown in the form of a solid rectangle, with a plurality of lengthwise edges 10, a plurality of width edges 12 and a plurality of thickness edges 14. Furthermore, as with any solid rectangle, there are shown upper and lower surfaces 16, 18, respectively. Also, side surfaces 20 are defined between thickness and width edges 14, 12. Upper surface 16 defines cross-slots 22, having stepped or V-shaped edges for accommodating slabs 24, for slidable engagement with cross-slots 22.

Additionally, bottom surface 18 of the solid rectangular invention structure defines a stepped or V-shaped edge lengthwise slot 26, into which is slidably engaged lengthwise slab 28.

Alternatively, the bottom surface of cross-slots 22 define grooves 30 for receiving and controlling set screws 32; and the upper surface of lengthwise slab 28 defines groove 34 for operation with and control of set screws 36.

Lengthwise slab 28 and lengthwise slot 26 cooperate to enable the separation of the invention structure at approximately its center as defined by edges 12a, about halfway between edges 12 at either end of the item in the lengthwise direction.

This latter, simple yet efficient lengthwise separation capability enables the accommodation of patients with bulging thighs.

In order to provide a more complete and detailed description of the present invention, a series of use and operation steps are now provided. A doctor of chiropractic treatment places the patient on a treatment table or the like in a relaxed position on the patient's belly. The structure, according to the present invention, is placed beneath the patient's heels, so that the left and right legs of the patient abut slabs 24 (see FIG. 5). Slides 24 are moved appropriately in order to accommodate leg length differences, and indicia 38 defined by cross-slabs 24 are used to quantify the leg lengths and/or the difference in leg lengths. In the alternative embodiment, set screws 32 are used to fix the cross-slabs in appropriate position for the patient, so that the structure according to the present invention is lifted and thereby better viewed by the doctor of chiropractic or other practioner making use of the tool.

In keeping with either or both of the above embodiments, when the patient has sufficient thigh size or other size to warrant, lengthwise slab 28 and slot 26 are used to separate the tool at approximately its center in order to accommodate such size or bulging thighs. Set screws 36 and grooves 34 are used to set the separation, as needed. Of course, in the drawings, set screws 36 are shown protruding through the upper surface of the tool and into groove 34 in lengthwise slab 28. Alternatively, set screws 36 are projecting through lengthwise slab 28 (which define holes for such purposes), and groove 34 is defined at the base of slot 26. Likewise, as an alternative, set screws 32 are made to project upwardly from upper surface 24 in order to present a grip for the practioner's thumb and forefinger. Also alternatively, the set screw type of structure is eliminated or used only as a stop structure with or without the grooves, and/or press fits are provided for all slides and slots.

In keeping with the foregoing, a tool for analyzing and measuring leg length differences is provided, but the invention is only to be limited by the following claims.

What is claimed is:

1. A leg length analyzer tool for measuring differences in a patient's leg lengths comprising a generally solid rectangular structure having end surfaces, an upper surface and a lower surface, said upper surface defining a pair of separated cross-slots, a pair of cross-slabs for slidable engagement each with one of said cross-slots, each of said slabs being a generally solid rectangular shape having a top surface defining indicia for measuring, said lower surface defining a lengthwise slot generally perpendicular to each of said cross-slots, and a lengthwise, generally solid rectangular slab having a top surface, for slidable engagement with said lengthwise slot in order to further separate said cross-slots to accommodate the physicality of said patient, all adapted and arranged for measuring a difference in a patient's leg lengths by placing one of said cross-slabs to abut the end of the patient's longer leg, moving the other of said cross-slabs so that it extends from its cross-slot to abut the end of the patient's shorter leg, whereby the said indicia of said other cross-slab indicates a measurement of said difference.

2. The invention according to claim 1 wherein said slots are all stepped slots.

3. The invention according to claim 1 wherein said slots are all V-edged slots, said slabs have side edges at an angle with respect to said slab top surfaces.

4. The invention according to claim 1 wherein said cross-slots define grooves and set screws are provided to engage said grooves for setting said cross-slabs.

5. The invention according to claim 1 wherein said lengthwise slab defines a top surface, which in turn defines a groove, and a set screw is provided to engage said groove in said lengthwise slab for setting said separation.

* * * * *